United States Patent
Veasey et al.

(10) Patent No.: US 8,523,827 B2
(45) Date of Patent: *Sep. 3, 2013

(54) MEDICAMENT INJECTION APPARATUS

(75) Inventors: Robert Frederick Veasey, Warwickshire (GB); Robert Woolston, Warwick (GB); Shane Alistair Day, Warwick (GB); Christopher Nigel Langley, Warwickshire (GB)

(73) Assignee: DCA Design International Limited, Warwick (GB)

(*) Notice: Subject to any disclaimer, the term of this patent is extended or adjusted under 35 U.S.C. 154(b) by 736 days.

This patent is subject to a terminal disclaimer.

(21) Appl. No.: 10/315,163

(22) Filed: Dec. 10, 2002

(65) Prior Publication Data

US 2003/0114800 A1    Jun. 19, 2003

(30) Foreign Application Priority Data

Dec. 18, 2001   (GB) .................................. 0130138.1

(51) Int. Cl.
*A61M 5/00* (2006.01)
(52) U.S. Cl.
USPC .......................................... 604/246; 604/151
(58) Field of Classification Search
USPC ........... 604/131, 141, 890.1–892.1, 151–155, 604/246–256; 128/DIG. 1, DIG. 12, DIG. 13; 600/431–435
See application file for complete search history.

(56) References Cited

U.S. PATENT DOCUMENTS

| 3,858,581 | A | | 1/1975 | Kamen |
| 3,871,361 | A | | 3/1975 | Kamen |
| 5,728,074 | A | * | 3/1998 | Castellano et al. ........... 604/207 |
| 5,755,692 | A | | 5/1998 | Manicom |
| 5,989,221 | A | | 11/1999 | Hjertman |
| 6,248,090 | B1 | | 6/2001 | Jensen et al. |
| 6,620,133 | B1 | * | 9/2003 | Steck ............................ 604/131 |
| 2003/0114801 | A1 | | 6/2003 | Woolston et al. |

FOREIGN PATENT DOCUMENTS

| EP | 0 293 958 A1 | 12/1988 |
| EP | 0 362 484 A | 4/1990 |
| WO | WO 97/14459 A1 | 4/1997 |
| WO | WO 97/30742 | * 8/1997 |
| WO | WO 99/15214 | 4/1999 |

* cited by examiner

*Primary Examiner* — Kevin C Sirmons
*Assistant Examiner* — Phillip Gray
(74) *Attorney, Agent, or Firm* — Oliff & Berridge, PLC

(57) ABSTRACT

A medicament injection apparatus that permits injection of a fluid medicament into a patient through a needle. The medicament injection apparatus includes a timer and a display, the timer being actuated upon commencement of an injection operation, in which the timer runs to a predetermined time until completion of the injection operation and the display is operated while the timer runs. Thus, informing a user of when a required period for dispersal of an injected medicament has lapsed so that the user knows when to withdraw a needle from the body after the injection.

12 Claims, 2 Drawing Sheets

MEDICAMENT INJECTION APPARATUS

FIELD OF THE DISCLOSURE

The disclosure relates to a medicament injection apparatus. In particular, but not exclusively, the disclosure has application in relation to electronically controlled medicament injection apparatus.

BACKGROUND

There is known from WO97/30742 a medicament injection apparatus in which a button is operated to inject a set dose of medicament through a needle unit. A switch is operated to cause a stopwatch to be set and started when the switch is operated. The medicament injection apparatus further includes a display. A number of seconds are counted and displayed from the moment an injection stroke is completed to allow a user to ensure that the needle remains inserted some seconds after the end of the injection. This is desirable since if the needle is withdrawn before the injected medicament has properly dispersed locally from the injection site within a patient, the injected medicament may escape through the needle wound and not be dispersed into the patient.

Unfortunately, particularly where a patient uses a medicament injection apparatus to self-administer medicament, it is common for the user to become impatient and withdraw the needle when the user feels a suitable period has elapsed. It is often the case that the suitable period is less than the required period for dispersal of the medicament resulting in the problem identified above.

It is an advantage of one aspect of the disclosure that this problem is substantially alleviated, or at least reduced.

SUMMARY

According to one embodiment of the disclosure, a medicament injection apparatus comprising a timer and a display in which the timer is actuated upon commencement of an injection operation, in which the timer runs to a predetermined time subsequent to completion of the injection operation and the display is operated while the tuner runs.

In other words, the user is not shown any indication of the injection operation. Thus, when the display stops, the user may safely withdraw the needle. Since the user does not know when the injection operation has stopped, the user cannot guess when the needle may be withdrawn without the identified problem arising.

Preferably, the display comprises a plurality of icons being alternately switched away from and back to a predetermined condition while the timer runs.

More preferably each of the plurality of icons is switched away from and back to the predetermined condition in a predetermined sequence.

Most preferably, the predetermined condition of the first icons is an "on" condition with each of the plurality of first icons being switch off and then on again in a predetermined sequence.

Preferably each of the plurality of icons is switched away from and back to the predetermined condition for a predetermined amount of time. The predetermined period of time typically comprises a fraction of a second.

BRIEF DESCRIPTION OF THE DRAWINGS

The disclosure will now be described, by way of example only, with reference to the accompanying drawings, in which.

DETAILED DESCRIPTION OF THE EMBODIMENTS

Figure 1:
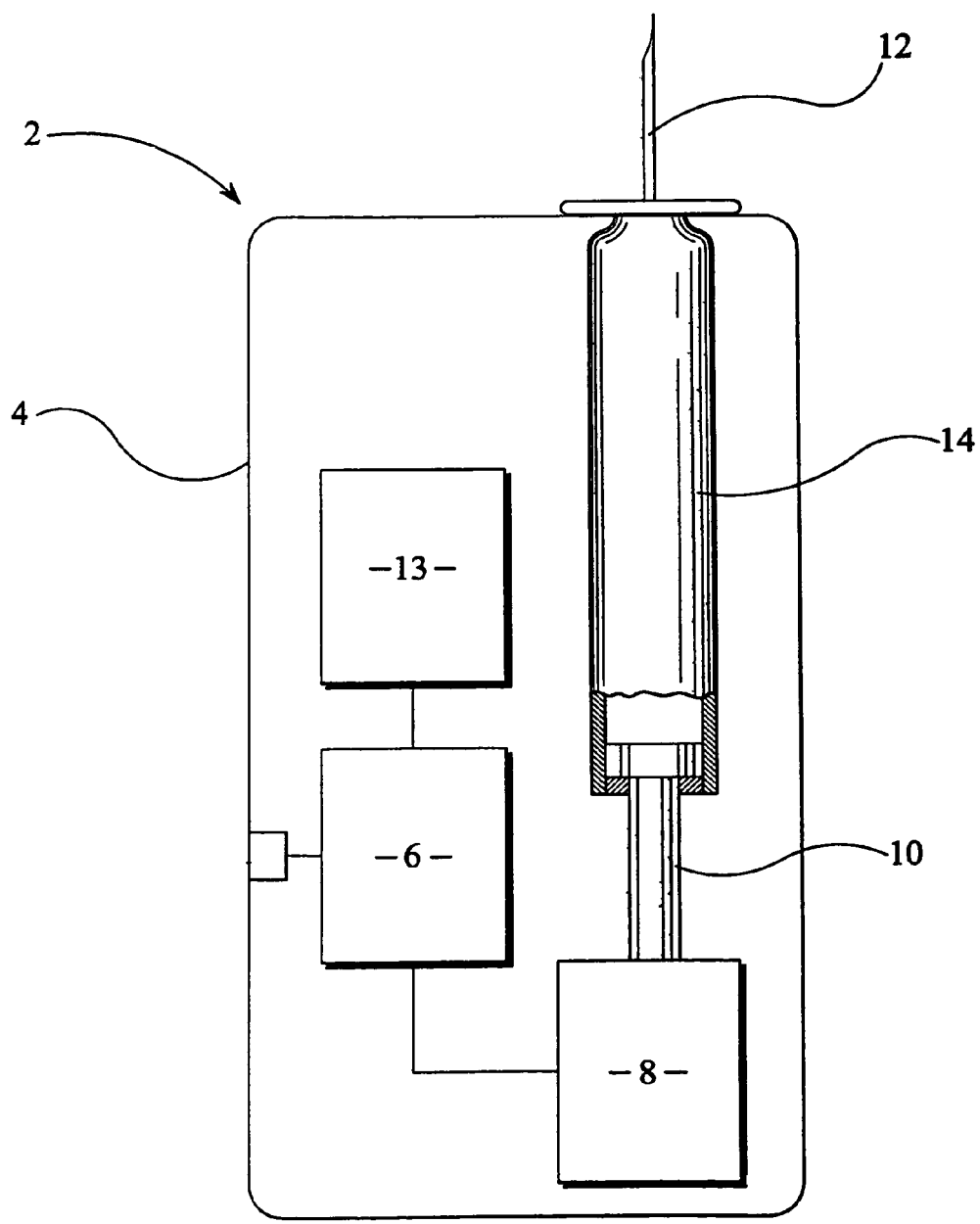
FIG. 1 shows a schematic view of a medicament injection apparatus in accordance with the disclosure.

Referring to FIG. 1, a schematic arrangement of a medicament injection device according to the disclosure is disclosed. The medicament injection device 2 comprises a housing 4, a control unit or microprocessor 6, a drive means 8, a piston 10, a needle unit 12 and a display 13.

A medicament cartridge 14, which is preferably replaceable, is located between the piston 10 and the needle unit 12. The medicament cartridge 14 includes a closure at a first end adapted to be pierced by the needle unit and a moveable plunger located towards a second end of the medicament cartridge and adapted to be driven by the piston 10 towards the first end of the medicament cartridge 14.

The control unit or microprocessor 6 includes a timer associated therewith. In use, a dosage of medicament to be injected is set. The drive means 8 is then actuated to drive the piston 10. The drive means 8 may be actuated mechanically or under the control of the control unit or microprocessor 6. Medicament from within the medicament cartridge 14 is then expelled from the medicament injection device 2.

The timer is actuated upon commencement of an injection operation. The timer is allowed to run to a time subsequent to completion of the injection operation and the display is operated while the timer runs. The time subsequent to completion of the ejection operation is a time sufficient to allow the injected medicament adequately to disperse locally from the injection site within the patient. An indication of time passing as the timer runs is provided on the display 13.

Figure 2:
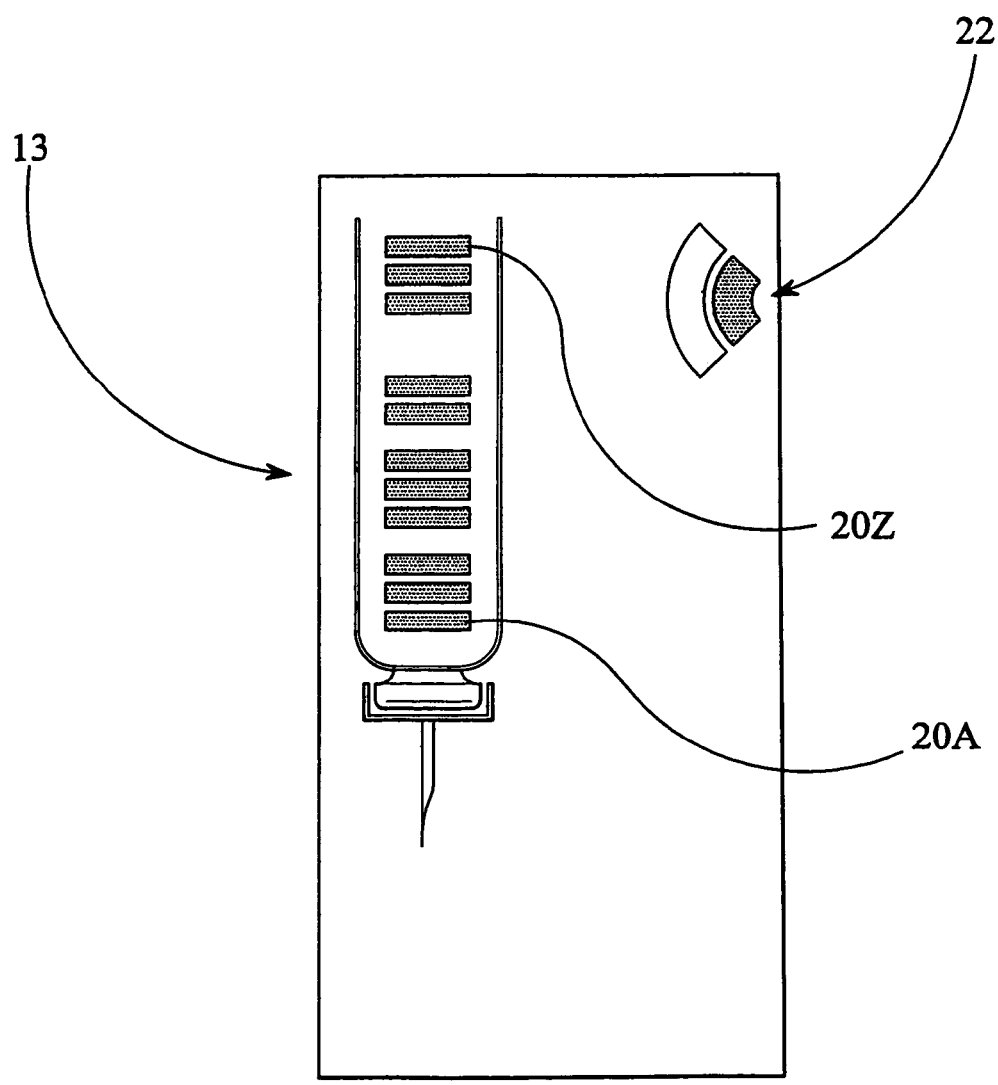
FIG. 2 shows a display suitable for use with a medicament injection apparatus in accordance with the disclosure.

Referring now to FIG. 2, there is shown a display 13 for use with the present invention. The display 13 includes a plurality of first icons 20A-20Z each of which may be turned on and off from a predetermined condition under the control of the microprocessor 6.

The display 13 may also include further icons 22 to provide an indication of further parameters including, but not being limited to, the size of the dosage to be injected, a clock and/or an error message.

In a preferred embodiment, before an injection operation begins all of the plurality of first icons 20A-20Z are turned on. This represents the predetermined condition of the first icons. When the timer starts a lowermost of the first icons 20A is turned off briefly. When this icon 20A has been turned back on, the icon 20B above is then turned off briefly. This process is repeated until the uppermost first icon 20Z is turned off briefly. This icon 20Z is then turned back on, and the lowermost first icon 20A is once again turned off briefly.

The above sequence continues for as long as the timer runs.

Each of the plurality of first icons 20A-20Z may be turned off for as long as is desired. However a short period, for example a fraction of a second, has been found useful in the production of a cycling display.

It will be understood that the plurality of first icons 20A-20Z may take other shapes and be disposed in other arrangements.

In an alternative embodiment, all of the first icons 20A-20Z may be briefly be turned on and off together to confirm to the user that the injection operation is about to commence.

In an alternative embodiment, the predetermined condition of the first icons may be an off condition, in which the appearance of a cycling display is produced by individual icons being switched on and then turned off in sequence.

What is claimed is:

1. A medicament injection apparatus suitable for the self-administration of a medicament, comprising:

a display; and a timer, the timer being actuated upon commencement of an injection operation, wherein the timer runs to a predetermined time following completion of the injection operation, the predetermined time following completion of the injection operation being a time sufficient to allow the injected medicament adequately to disperse locally from an injection site within a patient, and the display operates while the timer runs;

wherein the display runs from the commencement of the injection operation without any indication of the completion of the injection operation until said predetermined time has elapsed and then stops, thereby indicating to the user when to remove a needle from a body of the user after said dispersion of the injected medicament; and the timer and the display automatically stop upon expiration of the predetermined time.

2. The medicament injection apparatus according to claim 1, wherein the display comprises a plurality of icons being alternately switched away from and back to a predetermined condition while the timer runs.

3. The medicament injection apparatus according to claim 2, wherein each of the plurality of icons is switched away from and back to the predetermined condition in a predetermined sequence.

4. The medicament injection apparatus according to claim 2, wherein the predetermined condition of the icons is an "on" condition with each of the plurality of icons being switched off and then on again in a predetermined sequence.

5. The medicament injection apparatus according to claim 3, wherein the predetermined condition of the icons is an "on" condition with each of the plurality of icons being switched off and then on again in a predetermined sequence.

6. The medicament injection apparatus according to claim 2, wherein each of the plurality of icons is switched away from and back to the predetermined condition for a predetermined amount of time.

7. The medicament injection apparatus according to claim 3, wherein each of the plurality of icons is switched away from and back to the predetermined condition for a predetermined amount of time.

8. The medicament injection apparatus according to claim 1, wherein the display confirms to the user that the injection operation is about to commence and then runs without any indication of the completion of the injection operation until said predetermined time has elapsed.

9. The medicament injection apparatus according to claim 1, wherein the display is a cycling display.

10. The medicament injection apparatus according to claim 3, wherein the display is a cycling display, said predetermined sequence is repeated until the predetermined time has elapsed and then stops.

11. The medicament injection apparatus according to claim 7, wherein the display is a cycling display, said predetermined sequence is repeated until the predetermined time has elapsed and then stops.

12. The medicament injection apparatus according to claim 11, wherein the predetermined amount of time for which each of the plurality of icons is switched away from and back to the predetermined condition is a fraction of second.

* * * * *